(12) United States Patent
Szewczyk et al.

(10) Patent No.: US 10,045,927 B2
(45) Date of Patent: Aug. 14, 2018

(54) ORAL CARE COMPOSITIONS WITH REDUCED SURFACE STAINING

(71) Applicant: COLGATE-PALMOLIVE COMPANY, New York, NY (US)

(72) Inventors: Gregory Szewczyk, Flemington, NJ (US); Neeta A. Patel, Monmouth Junction, NJ (US); Suzanne Jogun, Wayne, NJ (US); Shashank Potnis, Thane (IN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/107,562

(22) PCT Filed: Dec. 10, 2014

(86) PCT No.: PCT/US2014/069471
§ 371 (c)(1),
(2) Date: Jun. 23, 2016

(87) PCT Pub. No.: WO2015/100010
PCT Pub. Date: Jul. 2, 2015

(65) Prior Publication Data
US 2016/0324753 A1    Nov. 10, 2016

(30) Foreign Application Priority Data

Dec. 23, 2013    (IN) .............. 3736/DEL/2013

(51) Int. Cl.
| | | |
|---|---|---|
| *A61Q 11/00* | (2006.01) | |
| *A61K 47/38* | (2006.01) | |
| *A61K 9/70* | (2006.01) | |
| *A61K 8/73* | (2006.01) | |
| *A61K 8/34* | (2006.01) | |
| *A61K 8/46* | (2006.01) | |
| *A61K 8/49* | (2006.01) | |
| *A61K 8/02* | (2006.01) | |
| *A61K 8/21* | (2006.01) | |

(52) U.S. Cl.
CPC ............ *A61K 8/731* (2013.01); *A61K 8/0241* (2013.01); *A61K 8/0254* (2013.01); *A61K 8/21* (2013.01); *A61K 8/345* (2013.01); *A61K 8/463* (2013.01); *A61K 8/4993* (2013.01); *A61Q 11/00* (2013.01); *A61K 2800/41* (2013.01); *A61K 2800/412* (2013.01); *A61K 2800/43* (2013.01)

(58) Field of Classification Search
CPC .......... A61K 2800/43; A61K 2800/412; A61K 8/731; A61K 47/38; A61Q 11/00
See application file for complete search history.

(56) References Cited

U.S. PATENT DOCUMENTS

| | | | | |
|---|---|---|---|---|
| 4,264,579 A | * | 4/1981 | Carr ..................... | A61K 8/26 424/49 |
| 2004/0115137 A1 | * | 6/2004 | Verrall ................ | A61K 8/0208 424/48 |
| 2008/0160056 A1 | * | 7/2008 | Boyd .................... | A61K 8/042 424/401 |
| 2009/0186107 A1 | * | 7/2009 | Haber .................. | A61K 9/006 424/747 |

FOREIGN PATENT DOCUMENTS

| | | | | |
|---|---|---|---|---|
| EP | 1935395 A1 | * | 6/2008 | .......... A61K 8/0237 |
| WO | WO2005058265 | | 6/2005 | |
| WO | WO 2010146601 A1 | * | 12/2010 | ............. A61K 9/006 |
| WO | WO 2012002946 A1 | * | 1/2012 | ............... A61K 8/02 |
| WO | WO 2012087328 A1 | * | 6/2012 | ............... A61K 8/02 |
| WO | WO2013089759 | | 6/2013 | |
| WO | WO2013089760 | | 6/2013 | |
| WO | WO2013089761 | | 6/2013 | |
| WO | WO2013089762 | | 6/2013 | |
| WO | WO2014084813 | | 6/2014 | |
| WO | WO2014092738 | | 6/2014 | |

OTHER PUBLICATIONS

Corresponding International Search Report and Written Opinion for PCT/US2014/069471 dated Feb. 26, 2015.

* cited by examiner

*Primary Examiner* — Tracy Liu

(57) ABSTRACT

Surface staining can be minimized or eliminated by providing an oral care composition comprising a first film comprising a pigment; and optionally a second film; wherein the first film has a dissolution rate in aqueous media that is inversely proportional to its thickness, wherein the first film is in the form of a particle.

11 Claims, 2 Drawing Sheets

(12) United States Patent

ORAL CARE COMPOSITIONS WITH REDUCED SURFACE STAINING

CROSS-REFERENCE TO RELATED PATENT APPLICATIONS

The present application is a U.S. national stage application under 35 U.S.C. § 371 of PCT Application No. PCT/US2014/069471, filed Dec. 10, 2014 that claims priority to Indian Patent Application No. 3736/DELNP/2013, filed Dec. 23, 2013, the entireties of which are incorporated herein by reference.

BACKGROUND

It is recommended that children should brush their teeth for at least 45-60 seconds, and adults for at least 90 to 120 seconds. Most people, especially children, do not brush their teeth for a sufficient period of time to obtain maximum benefit, and moreover have difficulty accurately estimating the time necessary to brush the teeth.

Toothpastes comprising films, which deliver a color change signal after brushing for appropriate period of time, and optionally deliver an active ingredient during the brushing period have been described in the art, most notably in PCT/US2011/065308 (Colgate-Palmolive Company). These toothpastes encourage users to brush their teeth for a longer period of time.

However, a problem associated with the use of such toothpastes is the staining of surfaces when the toothpaste is disposed of (e.g. toothpastes which has been expectorated (spit out) into a sink). The staining is caused by the dissolution of any undissolved film left in the toothpaste as it is being disposed.

Therefore, there is still a need in the art for toothpastes comprising films which deliver a color change signal after brushing, but minimizes or eliminates the staining of surfaces when the toothpaste is disposed of.

BRIEF SUMMARY

Surprisingly, it has been found that surface staining can be minimized or eliminated by providing an oral care composition comprising a first film comprising a pigment; and optionally a second film; wherein the first film has a dissolution rate in aqueous media that is inversely proportional to its thickness, wherein the first film is in the form of a particle.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

Figure 1:
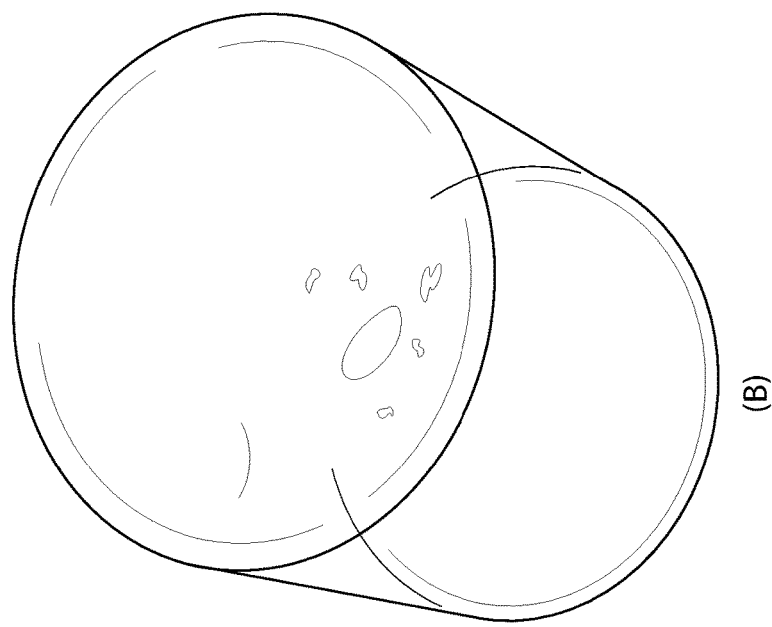
FIG. 1 depicts glass surface staining with a toothpaste with (A) 1.6 mm square film and (B) 30-50 mesh film.
Figure 1:
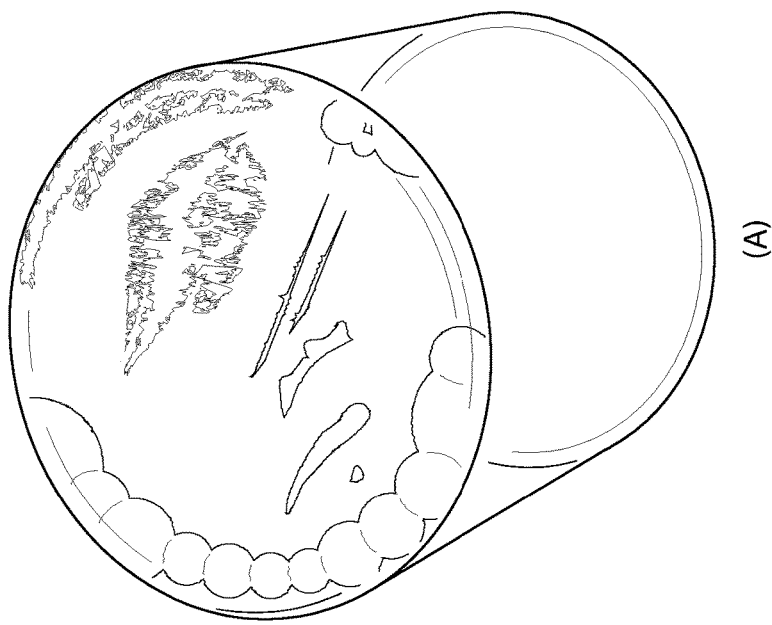

The following description of the preferred embodiment(s) is merely exemplary in nature and is in no way intended to limit the invention, its application, or uses.

Some embodiments of the present invention provide a dissolvable film (Film 1) comprising a cellulose ether, a plasticizer, a non-ionic surfactant and a pigment, wherein the film is in the form of a particle.

For the purposes of the invention, the term particle refers to smaller sizes or fragments of the film, e.g. the film is cut or ground into smaller sizes or fragments.

Various embodiments of the film include, but are not limited to:

1.1. Film 1 wherein the film comprises cellulose ethers, e.g., selected from
    (i) alkylcellulose, e.g., methylcellulose;
    (ii) hydroxyalkyl cellulose, e.g., selected from hydroxypropyl methyl cellulose, hydroxyethylpropyl cellulose, hydroxybutyl methyl cellulose, hydroxy propyl methyl cellulose, carboxymethyl cellulose and mixtures thereof;
    and (iii) mixtures thereof;
1.2. Any of the foregoing films comprising a starch, e.g. a pregelatinized starch;
1.3. Any of the foregoing films comprising a plasticizer, e.g, a polyalcohol, e.g., sorbitol, propylene glycol, glycerol, or low molecular weight polyethylene glycol, e.g., PEG 200;
1.4. Any of the foregoing films comprising propylene glycol, e.g., in an amount effective to provide plasticity to the film, e.g., about 20-30% by dry weight of the film;
1.5. Any of the foregoing films comprising a non-ionic surfactant or emulsifier, e.g., a polysorbate, e.g., polysorbate 80 (also known as polyoxyethylene(20) sorbitan monooleate, available commercially e.g., as Tween® 80), e.g., in an amount of about 1-5% by dry weight of the film;
1.6. Any of the foregoing films comprising a pigment, which can include, but is not limited to Pigment Blue 15 [147-14-8], Pigment Blue 15:2, Pigment Green 7 [1328-53-6], Pigment Orange 5 [3468-63-1], Pigment Red 4 [2814-77-9], Pigment Red 5 [6410-41-9], Pigment Red 48:4 [5280-66-0], Pigment Red 53:1 [5160-02-1], Pigment Red 57 [5858-81-1]. Pigment Red 57:1 [5281-04-9]; Pigment Red 57:2 Barium Lake [17852-98-1], Pigment Red 63:1 [6417-83-0], Pigment Red 64:1 [6371-76-2], Pigment Red 68 [5850-80-6], Pigment Red 83, Pigment Red 90:1 Aluminum Lake [16508-80-8], Pigment Red 112 [6535-46-2], Pigment Red 172 Aluminum Lake [12227-78-0], Pigment Red 173 Aluminum Lake, Pigment Violet 19 [1047-16-1], Pigment Yellow 1 [2512-29-0], Pigment Yellow 3 [6486-23-3], Pigment Yellow 12 [6358-85-6], Pigment Yellow 13 [5102-83-0], Pigment Yellow 73 [13515-40-7] or a combination of any of these pigments.
1.7. Any of the foregoing films comprising which is substantially dissolved after a period of greater than 30 seconds and less than 180 seconds of brushing, scrubbing or agitation in the oral cavity or on the skin in the presence of water;
1.8. Any of the foregoing films wherein the particle size is within a range selected from the group consisting of 10-100 mesh (0.0059-0.0787 inch), 20-80 mesh (0.0070-0.0331 inch); 25-60 mesh (0.0098-0.0278 inch) and 30-50 mesh (0.0117-0.0234 inch)—note: 1 mil=0.001 inch;
1.9. Any of the foregoing films, wherein the pigment of the film particle is released upon dissolution of the film particle thereby changing the color of the toothpaste after brushing for a period of 30-180 seconds, e.g., about 45-60 seconds in a toothpaste for use by a child or about 90-120 seconds in a toothpaste for use by an adult, thereby releasing the pigment and providing a color signal to the user of adequate brushing;

- 1.10. Any of the foregoing films comprising, by dry weight of the film, 20-60% cellulose ethers; 10-30% plasticizer; 1-5% non-ionic surfactant; and 15-55% pigment;
- 1.11. Any of the foregoing films comprising, by dry weight of the film, 20-60% cellulose ethers selected from methyl cellulose, hydroxypropylmethyl cellulose, and mixtures thereof; 10-30% propylene glycol; 1-5% polysorbate 80; and 15-55% pigment;
- 1.12. Any of the foregoing films wherein film further comprises an active is selected from flavors, fragrances, antibacterial agents, aesthetic agents or combinations thereof;
- 1.13. Any of the foregoing films which are topically acceptable;
- 1.14. Any of the foregoing films which are orally acceptable;
- 1.15. Any of the foregoing films comprising an antibacterial agent; in one embodiment of the invention, the antibacterial agent is selected from triclosan and essential oils from plant extracts, e.g., menthol.

The films of the invention are able to achieve sufficient release of the pigment in the oral cavity, but are surprisingly removed quickly when the film is disposed of onto a surface area and rinsed away.

The invention also provides a product (Product 1) which comprises a dissolvable film (Film 1) comprising a cellulose ether, a plasticizer, a non-ionic surfactant and a pigment, wherein the film is in the form of a particle as described above.

- 1.16. Product 1 wherein the product is a an oral care product, an oral care product, e.g., a dentifrice, for example a toothpaste, e.g., a clear gel or opaque toothpaste, comprising Film 1 described above;
- 1.17. Product 1 of 1.16 wherein the product is a clear gel or opaque toothpaste and the pigment of the film particle is released upon dissolution of the film particle thereby changing the color of the toothpaste after brushing for a period of 30-180 seconds, e.g., about 45-60 seconds in a toothpaste for use by a child or about 90-120 seconds in a toothpaste for use by an adult, thereby releasing the pigment and providing a color signal to the user of adequate brushing;
- 1.18. Any of the foregoing products wherein the product further contains an active agent, which includes, but is not limited to a flavoring, an aesthetic, an antibacterial agent, an amino acid, a fluoride source, a whitening agent, a zinc compound and mixtures thereof.
- 1.19. Any of the foregoing products wherein the product is a hand or body soap;
- 1.20. Any of the foregoing products wherein the product is a chewing gum;
- 1.21. Any of the foregoing products which is a chewing gum wherein the different actives are different flavorings, such that the chewing gum changes flavor over time.
- 1.22. Any of the foregoing products wherein the product further comprises an anionic surfactant, which includes but is not limited to water-soluble salts of $C_{8-20}$ alkyl sulfates, sulfonated monoglycerides of $C_{8-20}$ fatty acids such as the sodium salt of the monsulfated monoglyceride of hydrogenated coconut oil fatty acids, sarcosinates, taurates and mixtures thereof. Illustrative examples of these and other surfactants are higher alkyl sulfates such as sodium lauryl sulfate, sodium coconut monoglyceride sulfonate, sodium lauryl sarcosinate, sodium lauryl isoethionate, sodium laureth carboxylate, alkyl aryl sulfonates such as sodium dodecyl benzenesulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, amides are N-lauroyl sarcosine, and the sodium, potassium, and ethanolamine salts of N-lauroyl, N-myristoyl, or N-palmitoyl sarcosine, and the like and mixtures thereof. In one embodiment of the invention, the anionic surfactant is sodium lauryl sulfate (SLS).
- 1.23. Any of the foregoing products wherein the amount of anionic surfactant is in a range selected from the group consisting of in an amount from 1.5 wt. % to 5.0 wt. %. and 1.5 wt. % to 2.0 wt. %.
- 1.24. Any of the foregoing products wherein the product further comprises an abrasive Abrasives such as silica, calcined alumina, sodium bicarbonate, calcium carbonate, dicalcium phosphate and calcium pyrophosphate may be included in the base dentifrice compositions used in the practice of the present invention. Other abrasives may also be suitable for use in the compositions described herein. Visually clear dentifrice compositions may be obtained by using an abrasive such as collodial silica, e.g., those sold under the trade designation Zeodent® available from the Huber Corporation or alkali metal aluminosilicate complexes (that is, silica containing alumina combined in its matrix) which have refractive indices close to the refractive indices of gelling agent-liquid (including water and/or humectant) systems used in dentifrice compositions.
- 1.25. Any of the foregoing products wherein the antibacterial agent includes, but is not limited to Triclosan (5-chloro-2-(2,4-dichlorophenoxy)phenol); 8-hydroxyquinoline and salts thereof, zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; magnolia extract; grapeseed extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; and mixtures thereof.
- 1.26. Any of the foregoing products wherein the product further comprises an amino acid (unless otherwise specified, include free amine and salt forms). In one embodiment of the invention, the amino acid is selected from the group consisting of arginine, cysteine, leucine, isoleucine, lysine, alanine, asparagine, aspartate, phenylalanine, glutamate, glutamic acid, threonine, glutamine, tryptophan, glycine, valine, praline, serine, tyrosine, and histidine, and a combination of two or more thereof. In another embodiment of the invention, the 1.27. Any of the foregoing products wherein the product further comprises a fluoride source. In one embodiment, the fluoride source selected from stannous fluoride, sodium fluoride, potassium fluoride, sodium monofluorophosphate, sodium fluorosilicate, ammonium fluorosilicate, amine fluoride, ammonium fluoride, and mixtures thereof.

1.28. Any of the foregoing products wherein the product further comprises a whitening agent. In one embodiment, the whitening agent is a peroxide (which includes, but is not limited to hydrogen peroxide or urea peroxide), peroxy acids, or a non-peroxide compound (which includes, but is not limited to high cleaning silicas, chlorine dioxide, chlorites, hypochlorites and colorants (such as titanium dioxide and hydroxyapatite)).

1.29. Any of the foregoing products wherein the product further comprises a zinc compound. In one embodiment, the zinc compound is selected from the group consisting of zinc acetate, zinc borate, zinc butyrate, zinc carbonate, zinc citrate, zinc formate, zinc gluconate, zinc glycerate, zinc glycolate, zinc lactate, zinc oxide, zinc phosphate, zinc picolinate, zinc proprionate, zinc salicylate, zinc silicate, zinc stearate, zinc tartrate, zinc undecylenate and mixtures thereof The invention provides, in another embodiment, a method of improving post-use disposal of an oral care composition containing a pigment to be released during use which comprises adding a film as described above during the process of making the oral care composition wherein post-use disposal of the oral care composition does not stain the surface of the disposal area.

In another embodiment of the method, the process of making the oral care composition further comprises adding an anionic surfactant in an amount from 1.5 wt. % to 5.0 wt. %. and 1.5 wt. % to 2.0 wt. %. In another embodiment of this aspect of the invention, the anionic surfactant is sodium lauryl sulfate.

In some embodiments, substantially all of the pigment is released at one time. As used herein, the term "substantially all" refers to greater than 90% of the total amount of pigment contained in the film. In some embodiments, the first film releases at least 90% of the total amount of pigment contained therein, at a particular point in time. In some embodiments, the first film releases greater than 90% of the total amount of pigment contained therein, at a designated point in time. In some embodiments, the first film releases at least 91% of the total amount of pigment contained therein, at the designated point in time. In some embodiments, the first film releases at least 95% of the total amount of pigment contained therein, at the designated point in time. In some embodiments, the first film releases at least 96% of the total amount of pigment contained therein, at the designated point in time. In some embodiments, the first film releases at least 97% of the total amount of pigment contained therein, at the designated point in time. In some embodiments, the first film releases at least 98% of the total amount of pigment contained therein, at the designated point in time. In some embodiments, the first film releases at least 99% of the total amount of pigment contained therein, at the designated point in time.

Orally acceptable or topically acceptable: The compositions of the invention are intended for topical use in the mouth or on the skin, thus components for use in the present invention should be orally acceptable, that is, safe for topical use in the mouth, in the amounts and concentrations provided.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Embodiments of the present invention are further described in the following examples. The examples are merely illustrative and do not in any way limit the scope of the invention as described and claimed.

EXAMPLES

Example 1—Embodiment of the Film of the Invention

The films of the invention can be prepared as follows. Approximately fifty percent of the required film formula water is weighed out and heated as necessary depending on the polymer type. Polymers (HPMC, MC, etc) are slowly added to the water under mixing conditions and the polymers are allowed to disperse and hydrate for 10-15 minutes. Additional water up to the full amount is added until the slurry has the consistency of honey. Plasticizers and surfactants should then be added while mixing and allowed to mix for 5 minutes. Other particles such as dyes, pigments, etc. should then be added to the mixture and allowed to mix for 10 additional minutes. The slurry should then be de-aerated. Films can then be cast and dried from the slurry to the desired thickness typically 1-10 mils.

These procedures resulted in 30-50 mesh film particles which comprised of:

TABLE 1

| Component | wt. % |
|---|---|
| HPMC (hydroxypropylmethylcellulose) | 48.2 |
| Propylene glycol | 18.0 |
| Tween 80 (polyoxyethylene (20) sorbitan monooleate) | 3.8 |
| Pigment | 30.0 |
| Total | 100.0 |

Example 2—Incorporation of the Film Particles into an Oral Care Composition

The film particles from Example 1 were incorporated into a liquid toothpaste which is described below in Table 2

TABLE 2

| Component | wt. % |
|---|---|
| Sodium fluoride | 0.1-1.0 |
| Sodium saccharin | 0.1-0.5 |
| Glycerin | 20-40 |
| Xanthan gum | 0.25-1 |
| Carrageenan (iota) | 0.25-1 |
| Sorbitol | 10-30 |
| Propylene glycol | 0.25-1 |
| Gantrez ® (Polymethylvinylether/maleic anhydride copolymer | 10-20 |
| NaOH (50% solution) | 0.5-2.0 |
| Titanium dioxide | 0.05-0.20 |
| Zeodent ® 105 (synthetic amorphous silica) | 5-15 |
| Zeodent ® 114 (synthetic amorphous silica) | 5-15 |
| Zeodent ® 165 (synthetic amorphous silica) | 1-5 |
| Sodium lauryl sulfate (SLS) | 1-2 |
| Mica | 0.5-1.0 |
| Film particles | 0.20 |
| Triclosan | 0.1-0.5 |
| Flavor | 0.5-2 |
| Water | q.s |
| Total | 100.00 |

Example 3—Procedure for Estimating Film Depreciation and Resulting Surface Staining 10-50 g of liquid toothpaste from Example 2 are placed into a scintillation vial. A sufficient quantity of film particles described in Example 1 is added to the liquid toothpaste and visually evaluated (typically 0.2% or less). The liquid toothpaste and film is shaken vigorously by hand for 15 seconds and placed on a benchtop. The initial distribution and quantity on bottom of vial is noted before starting the timer. The liquid toothpaste and film is visually inspected and the percentage of film deprecating over time is recorded. At completion, the contents of the scintillation vial is emptied into a sink. The scintillation vial is place under the tap and water is permitted to flow for 10 seconds from the tap. The scintillation vial is drained and then inverted. The difference in the amount of film residue left behind is recorded.

Example 4—Comparison of Film Settling and Residual Staining

The amount of film settling was compared for a toothpaste of the invention which has a ground film particles of 30-50 mesh with a comparative toothpaste with film of 1.6 mm (approx. 12 mesh) thick squares (toothpaste of PCT/US2011/065308). As can be seen from the data in Table 3 below, the amount of film setting after 10 minutes was drastically reduced.

TABLE 3

Amount of film settling in 3:1 slurries of toothpaste in water

| | t = 0 | t = 1-2 min. | t = 5 min. | t = 10 min. |
|---|---|---|---|---|
| 1.6 mm film squares (approx. 12 mesh) | 10% | 50% | 75% | 100% |
| Ground film particles (30-50 mesh) | 0% | <5% | 5% | 10% |

FIG. 1 depicts a glass surface after 20 minutes of settling and subsequent rinsing. Surface (A) was exposed to the toothpaste slurry with 1.6 mm square film whereas surface (B) was exposed to the toothpaste slurry with ground film 30-50 mesh. As can be seen from the figure, surface (A) shows significant staining compared to surface (B). While not wishing to be bound by theory, it is believed that the residual films which have smaller size film particles have increased buoyancy and are therefore easier to rinse away with water before residual staining is observed, i.e. the release of pigment from the discarded film particles onto a surface.

Example 5—Effect of Anionic Surfactant on Film Settling

The film particles described in Example 1 were incorporated into a toothpaste composition with the formula described in Table 4 below.

TABLE 4

| Component | wt. % |
|---|---|
| Sodium fluoride | 0.12-0.36 |
| Sodium saccharin | 0.25-0.35 |
| Glycerin | 25-35 |
| Xanthan gum | 0.3-0.7 |
| Carrageenan (iota) | 0.3-0.7 |
| Sorbitol | 15-25 |
| Propylene glycol | 0.3-0.7 |
| Gantrez ® (Polymethylvinylether/maleic anhydride copolymer) | 12.5-17.5 |
| NaOH (50% solution) | 1.0-1.5 |
| Titanium dioxide | 0.075-0.125 |
| Zeodent ® 105 (synthetic amorphous silica) | 7.5-12.5 |
| Zeodent ® 114 (synthetic amorphous silica) | 7.5-12.5 |
| Zeodent ® 165 (synthetic amorphous silica) | 2-4 |
| Sodium lauryl sulfate (SLS) | 1.5-2.0 |
| Mica | 0.6-0.8 |
| Film particles | 0.20 |
| Triclosan | 0.2-0.4 |
| Flavor | 0.75-1.25 |
| Water | q.s |
| Total | 100.00 |

Example 6—Effect of Anionic Surfactant on Film Settling

Figure 2:
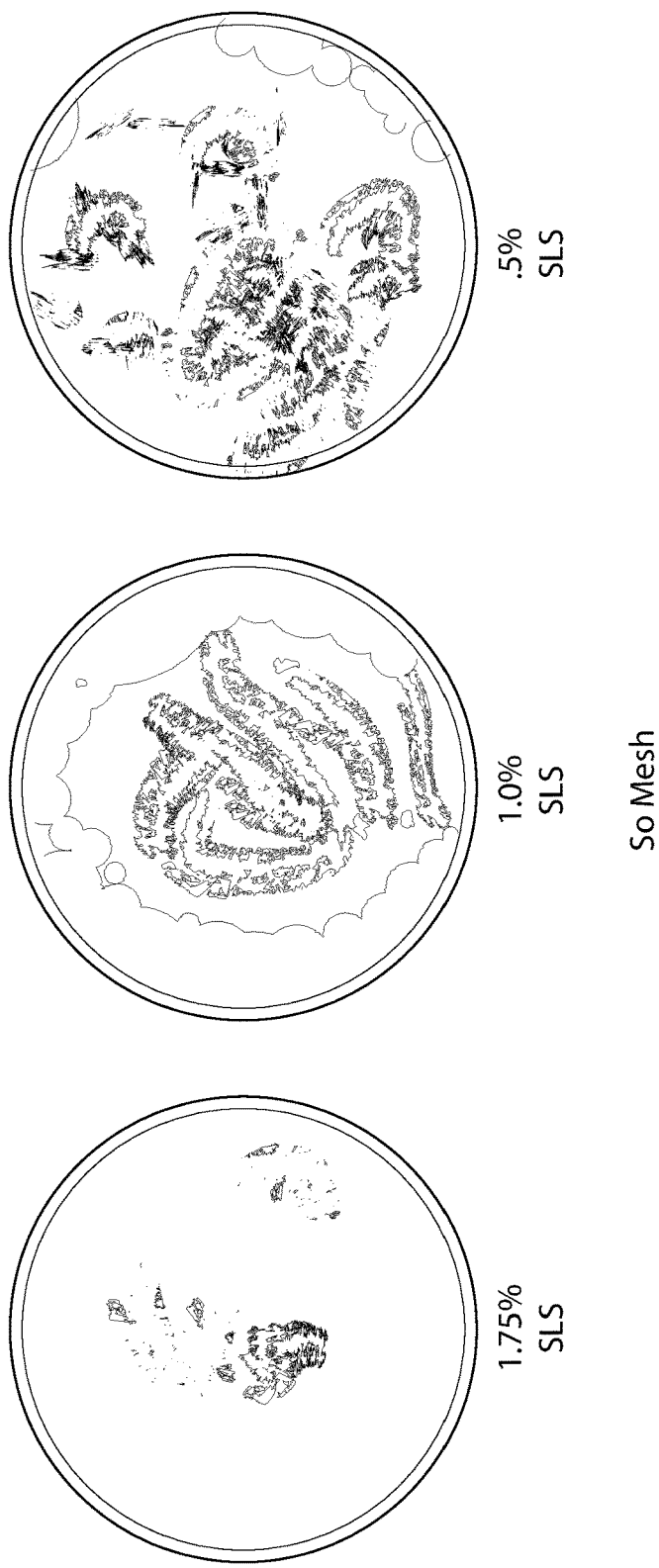
FIG. 2 depicts the effect of sodium lauryl sulfate (SLS) on film settling.

One of the embodiments of the invention was the further addition of an anionic surfactant to the film particle composition. FIG. 2 shows the effect of adding differing amounts of an anionic surfactant, e.g. sodium lauryl sulfate (SLS), to the oral care composition described by Example 5. Increasing the amount of SLS to about 1.75% resulted in significantly less residual staining by the pigment.

As those skilled in the art will appreciate, numerous changes and modifications may be made to the embodiments described herein without departing from the spirit of the invention. It is intended that all such variations fall within the scope of the appended claims.

What is claimed is:

1. A toothpaste composition comprising a single-layer film comprising, by dry weight of the film, 20-60 wt. % cellulose ether selected from alkylcellulose, hydroxyalkyl cellulose, and combinations thereof; 10-30 wt. % plasticizer selected from sorbitol, propylene glycol, glycerol, and polyethylene glycol; 1-5 wt. % non-ionic polysorbate surfactant; and 15-55 wt. % pigment;
   wherein the film is dissolved after a period of greater than 30 seconds and less than 180 seconds of brushing, scrubbing or agitation in the oral cavity in the presence of water; and the film is in the form of a particle having a size of 30 to 50 mesh.

2. The composition of claim 1 wherein the cellulose ether comprises a hydroxylalkyl cellulose.

3. The composition according to claim 1, wherein the cellulose ether comprises an alkylcellulose which comprises methylcellulose.

4. The composition according to claim 2, wherein the hydroxyalkyl cellulose is selected from: hydroxypropyl methyl cellulose, hydroxyethylpropyl cellulose, hydroxybutyl methyl cellulose, carboxymethyl cellulose and a combination of two or more thereof.

5. The composition according to claim 1, wherein the plasticizer comprises propylene glycol.

6. The composition according to claim 1, wherein the non-ionic polysorbate surfactant comprises polysorbate 80.

7. The composition according to claim 1, wherein the pigment comprises Pigment Blue 15 [147-14-8], Pigment Blue 15:2, Pigment Green 7 [1328-53-6], Pigment Orange 5 [3468-63-1], Pigment Red 4 [2814-77-9], Pigment Red 5 [6410-41-9], Pigment Red 48:4 [5280-66-0], Pigment Red 53:1 [5160-02-1], Pigment Red 57 [5858-81-1], Pigment Red 57:1 [5281-04-9]; Pigment Red 57:2 Barium Lake [17852-98-1], Pigment Red 63:1 [6417-83-0], Pigment Red 64:1 [6371-76-2], Pigment Red 68 [5850-80-6], Pigment Red 83, Pigment Red 90:1 Aluminum Lake [16508-80-8], Pigment Red 112 [6535-46-2], Pigment Red 172 Aluminum Lake [12227-78-0], Pigment Red 173 Aluminum Lake, Pigment Violet 19 [1047-16-1], Pigment Yellow 1 [2512-29-0], Pigment Yellow 3 [6486-23-3], Pigment Yellow 12 [6358-85-6], Pigment Yellow 13 [5102-83-0], Pigment Yellow 73 [13515-40-7] or a combination of any of these pigments.

8. The composition according to claim 1, wherein the film comprises, by dry weight of the film, 20-60 wt. % of a cellulose ether selected from methyl cellulose, hydroxypropylmethyl cellulose, and a combination thereof; 10-30 wt. % propylene glycol; 1-5 wt. % polysorbate 80; and 15-55 wt. % pigment.

9. The oral care composition of claim 1, wherein the composition further comprises an active agent selected from the group consisting of flavoring, an anesthetic, an antibacterial agent, an amino acid, a fluoride source, a whitening agent, a zinc compound and mixtures thereof.

10. The oral care composition of claim 1, wherein the oral care composition further comprises an anionic surfactant in an amount from 1.5 wt. % to 5.0 wt. %.

11. The oral care composition of claim 1, wherein the oral care composition further comprises an anionic surfactant in an amount from 1.5 wt. % to 2.0 wt. % and wherein the anionic surfactant is sodium lauryl sulfate.

* * * * *